United States Patent [19]
Cockburn

[11] Patent Number: 5,807,304
[45] Date of Patent: Sep. 15, 1998

[54] MEDICAL NEEDLE FOR USE IN ULTRASOUND IMAGING

[76] Inventor: John F. Cockburn, Roquebrune, Rue de lac Grouville, Jersey, JE3 6DR, United Kingdom

[21] Appl. No.: 775,225

[22] Filed: Dec. 31, 1996

Related U.S. Application Data

[63] Continuation-in-part of Ser. No. 706,986, Aug. 27, 1996, Pat. No. 5,728,124, which is a continuation of Ser. No. 401,625, Mar. 9, 1995, Pat. No. 5,549,112.

[51] Int. Cl.$^6$ .................................................. A61B 17/34
[52] U.S. Cl. ................................................................ 604/19
[58] Field of Search .................................... 600/459, 461, 600/462, 463, 464, 466, 467, 471; 604/22, 19, 20, 21

[56] References Cited

U.S. PATENT DOCUMENTS

| | | |
|---|---|---|
| 3,556,079 | 1/1971 | Omizo . |
| 4,411,657 | 10/1983 | Galindo . |
| 4,413,993 | 11/1983 | Guttman . |
| 4,790,830 | 12/1988 | Hamacher . |
| 4,838,877 | 6/1989 | Massau . |
| 5,046,503 | 9/1991 | Schneiderman ................ 128/662.06 |
| 5,095,910 | 3/1992 | Powers ............................ 128/662.05 |
| 5,131,394 | 7/1992 | Gehlbach ........................ 128/662.05 |
| 5,209,721 | 5/1993 | Wilk . |
| 5,360,416 | 11/1994 | Ausherman et al. . |
| 5,372,138 | 12/1994 | Crowley et al. ..................... 600/463 |
| 5,383,465 | 1/1995 | Lesny et al. ........................ 600/461 |
| 5,383,466 | 1/1995 | Partika ............................... 600/459 |
| 5,469,853 | 11/1995 | Law et al. .......................... 600/463 |

FOREIGN PATENT DOCUMENTS

| | | |
|---|---|---|
| 0083973 | 7/1983 | European Pat. Off. . |
| 0127781 | 5/1984 | European Pat. Off. . |
| 0278186 | 2/1987 | European Pat. Off. . |
| 0397960 | 11/1990 | European Pat. Off. . |
| 0453251 | 10/1991 | European Pat. Off. . |
| 1321205 | 1/1972 | United Kingdom . |
| 2044107 | 2/1980 | United Kingdom . |
| 2157828 | 10/1985 | United Kingdom . |
| 2255282 | 4/1991 | United Kingdom . |
| 2262238 | 12/1992 | United Kingdom . |
| 8203160 | 9/1982 | WIPO . |
| 9205816 | 9/1990 | WIPO . |

*Primary Examiner*—George Manuel
*Attorney, Agent, or Firm*—Richard J. Godlewski

[57] ABSTRACT

A medical needle 1 including a tubular stylet 30 has one or more apertures 32, 32$^{A-F}$ at its distal end 16, which are located and dimensioned to prevent occlusion by body tissue. The aperture may be formed by a convexly sided, transverse channel 32$^B$ cut into the needle wall 19 or can face rearwardly. Alternatively, a plurality of spaced, longitudinal slits 32$^C$ or circular apertures 32$^D$ can be provided by laser perforation. The needle can be associated with an outer cutting sheath 34 housing a trocar 21 for use in ultrasound imaging. In further embodiments, the needle can constitute the stylet of an aspiration biopsy needle (FIG. 8) or a needle assembly can comprise a stylet 130 within a cannula 140, the stylet having an expanded distal tip 133 of cross-section complimentary to that of the cannula bore so as to prevent occlusion of the cannula end by tissue (FIG. 7).

18 Claims, 3 Drawing Sheets

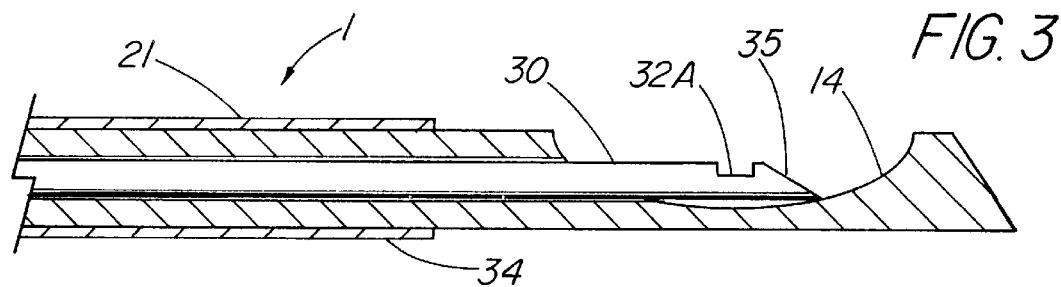
FIG. 3
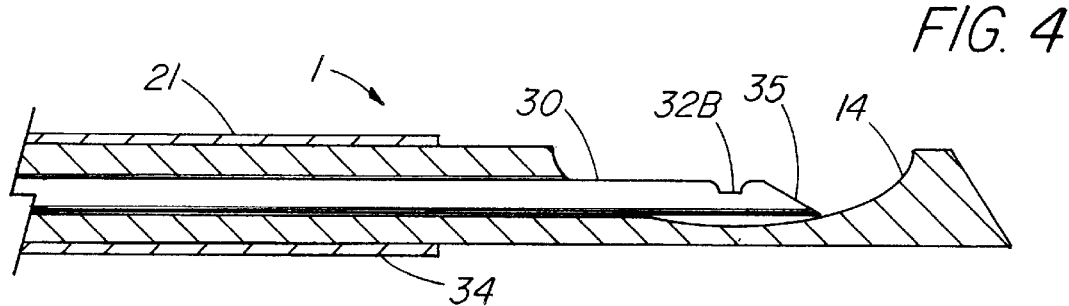
FIG. 4
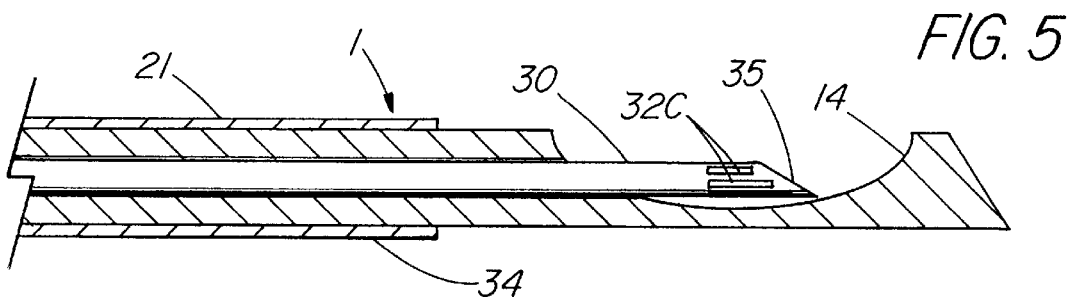
FIG. 5
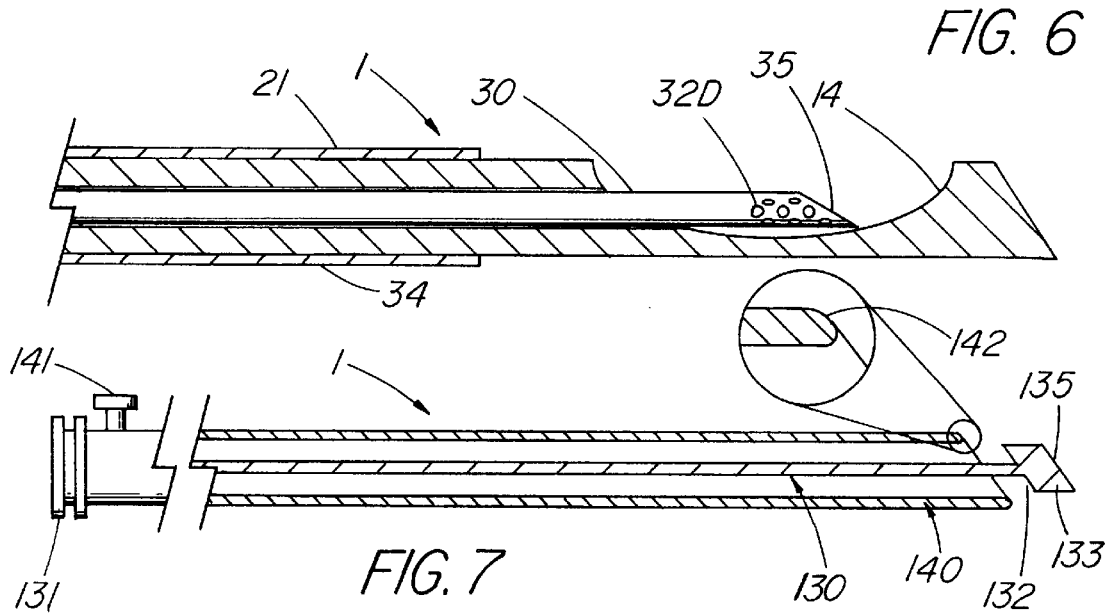
FIG. 6
FIG. 7

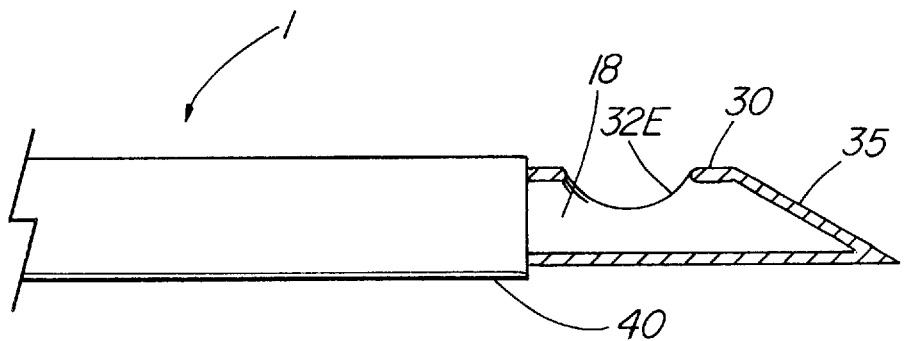
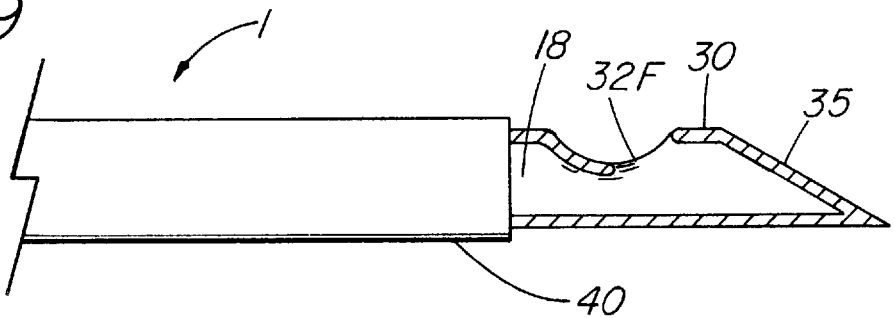
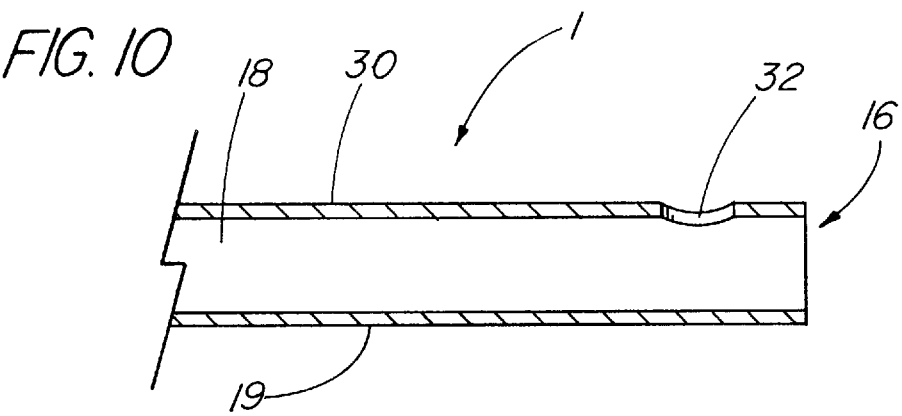

MEDICAL NEEDLE FOR USE IN ULTRASOUND IMAGING

CROSS-REFERENCE TO RELATED APPLICATIONS

This application is a continuation-in-part of application Ser. No. 08/706,986, filed Aug. 27, 1996, entitled "Medical Needle for Use in Ultrasound Imaging and Method of Enhancing the Visibility of Such a Needle to Ultrasound" now U.S. Pat. No. 5,728,124, which is a continuation of application Ser. No. 08/401,625, filed Mar. 9, 1995, entitled "Medical Needle for Use in Ultrasound Imaging and Method of Enhancing the Visibility of Such a Needle to Ultrasound," now U.S. Pat. No. 5,549,112.

TECHNICAL FIELD

The present invention relates to a medical needle for use in ultrasonic imaging.

BACKGROUND OF THE INVENTION

The theory of ultrasonic transmission in biopsy needles is discussed in ULTRASONICS Vol. 26, No. 1, 1988 pp 27 to 30.

U.S. Pat. No. 3,556,079 (Omizo) discloses a medical apparatus comprising a tubular needle within which is mounted an ultrasonic transducer, which may be a transmitter, a receiver or a combined transmitter and receiver. This transducer is coupled to saline solution within the needle and transmits and/or detects ultrasound at considerable distances through body tissue at a frequency of, e.g., 5 MHz, which is subsequently reflected off, e.g., flowing blood in a blood vessel and shifted in frequency according to the Doppler equation. If the transducer in the needle is a transmitter only, then an external ultrasound receiver is arranged to detect the reflected Doppler-shifted ultrasound, which is demodulated to generate an audio signal whose amplitude is a maximum when the needle is directed at the blood vessel. However, the above arrangement merely enables the position of the blood vessel or other target to be detected and does not enable the position of the needle to be detected. It cannot, for example, be used to direct a needle towards a portion of diseased static tissue. Furthermore, it is not an imaging system.

Ultrasound imaging utilizes the principle of sound reflectivity in order to form images of body organs. These images are displayed on the monitor in grey-scale. Some ultrasound machines also incorporate the principle of Doppler frequency shift, which allows moving objects, e.g., red blood cells in a blood vessel to be imaged. Such vessels can then be assigned a color according to the direction of movement within them, and they appear in color against the grey-scale background of their environs.

It is often desirable to form such an image during treatment with an aspiration or a biopsy needle, and it has been found difficult to produce a clearly defined image of the needle by this technique. It has been proposed to apply a transverse vibration to the needle in order to overcome this problem, but this does not result in a clear image of the needle tip.

GB-A-2,157,828 discloses an ultrasonic imaging apparatus comprising an inner needle having a miniature ultrasonic transducer mounted at its tip and an outer tubular puncture needle surrounding and supporting the inner needle. An ultrasonic imager generates an ultrasonic beam, which impinges on the miniature transducer, and the resulting electric output signal is either used to trigger a transponder, which causes the transducer to emit a predetermined ultrasonic signal, which is detectable and locatable by the imager or to enable circuitry in the imager to detect the position of the needle from the time interval between emission and detection of the ultrasonic beam. From this information, the position of the needle can be superimposed on the image. However, the above arrangement is complex and expensive, and, in general, the needle can be used only with one design of imager.

Further background information is provided in U.S. Pat. No. 5,131,394; EP-A-397,960; EP-A-083,973 (which teaches at page 7, paragraph 1, the desirability of contact between the stylet and the needle); and WO-A-82/03160, which, however, lies outside the technical field of the present invention.

EP-A-453,251 discloses a biopsy needle having a solenoid coil coupled to a core, which is mounted directly on the proximal end of the stylet and arranged to reciprocate the stylet longitudinally at a frequency of, e.g., up to 100 Hz in order to render the needle tip visible to Doppler ultrasound. The amplitude of vibration is such that the tip of the stylet oscillates between a position in which it is flush with the opening of the cannula and a position in which it is retracted about 1 mm into the cannula.

However, the above arrangement in which the vibratory transducer is directly coupled to the stylet has the disadvantage that movement of the stylet inevitably causes motion of similar amplitude and frequency in the cannula, with the result that the motion is not confined to the needle tip and the Color Doppler imager assigns a flare of color to the entire needle. Furthermore, the weight of the solenoid makes the needle harder to manipulate, an important point when one considers the degree of accuracy needed to perform certain biopsies.

U.S. Pat. No. 5,549,112; copending U.S. patent application Ser. No. 08/706,986, filed Aug. 27, 1996; and UK patent applications GB 9503548 and GB 2298368 (from which the present application claims priority) discloses and claims a medical apparatus comprising a tubular needle which is adapted for insertion into body tissue, the needle being provided with a transducer which is substantially mechanically isolated from the needle and coupled to a fluid column within the needle, the transducer being arranged to generate a longitudinal oscillation of the fluid column at a sub-ultrasonic (preferably audio) frequency, which enhances the visibility of the region of the needle tip to Doppler ultrasound imaging.

The above patent and applications disclose an apparatus in which the transducer is remote from the needle and is coupled to the needle by a flexible tube, which contains a further fluid column (preferably an air column) coupled to the transducer. The above apparatus was subsequently described by the present applicant in the May 1995 issue of *Radiology*. In a preferred embodiment disclosed in the above patent application, the needle comprises a tubular stylet, the stylet being located within a cannula or trocar and the transducer being coupled to a fluid column within the stylet and substantially isolated from the stylet.

SUMMARY OF THE INVENTION

The present invention is directed to a medical needle having an aperture at its distal end which communicates with its bore, the aperture being located and dimensioned to substantially prevent its occlusion by body tissue in use.

The invention also provides a medical needle assembly comprising a stylet within a cannula, the stylet having an expanded distal tip which tip has a transverse cross-section generally complementary to that of the bore of the cannula so as to substantially prevent the occlusion by body tissue of the distal end of the cannula in use, the stylet being advanceable relative to the cannula to define a radial aperture between the tip and the distal end of the cannula which communicates with the bore of the cannula.

For the avoidance of doubt, neither the hollow medical needle disclosed in my earlier UK patent application GB 9404863.4, which has a radial aperture at its proximal end and an open tubular distal end through which a solid stylet extends, nor the needle assembly disclosed in that UK patent application in which the cross-section of the distal tip of the stylet is not generally complementary to that of the bore of the cannula is considered to be within the scope of the present invention.

In a preferred embodiment of the present invention, the aperture is a radial aperture formed in a cylindrical wall of the needle. However, it is also envisaged that the aperture may face rearwardly.

The medical needle of the present invention can for example, comprise a hollow stylet in which the aperture is formed, and can optionally include a cannula or trocar in which the stylet is located.

Preferably the aperture has a non-cutting external edge region, which can for example, be defined by a convex transition region between the forward and/or rear region of the aperture and the adjacent forward and/or rear external surface of the needle wall.

Desirably the smallest dimension of the or each aperture is no greater than 2 mm, preferably no greater than 1 mm, and more preferably no greater than 0.5 mm.

The biopsy device of the present invention is particularly, but not exclusively, for use in the above-described apparatus of GB 9503548.1. For example, the needle of the invention (particularly when in the form of a stylet) can alternatively, be used to introduce alcohol from its aperture into a tumor to necrose the tumor.

BRIEF DESCRIPTION OF THE DRAWING

Preferred embodiments of the invention are described below by way of example only with reference to the accompanying drawings, wherein:

FIG. 3 is a longitudinal cross-section of still another needle in accordance with the invention for use in the arrangement of FIG. 1;

FIG. 4 is a longitudinal cross-section of yet another needle in accordance with the invention for use in the arrangement of FIG. 1;

FIG. 5 is a longitudinal cross-section of still yet another needle in accordance with the invention for use in the arrangement of FIG. 1;

FIG. 6 is a longitudinal cross-section of another needle in accordance with the invention for use in the arrangement of FIG. 1;

FIG. 7 is a side elevation, partly in cross-section of another needle in accordance with the invention;

FIG. 8 is a side elevation, partly in cross-section of an aspiration biopsy needle assembly in accordance with the invention;

FIG. 9 is a side elevation, partially in cross-section of a further aspiration biopsy needle assembly in accordance with the invention; and FIG. 10 is an enlarged and sectioned side view of the distal end of the tubular stylet of FIG. 2.

DETAILED DESCRIPTION

Figure 1:
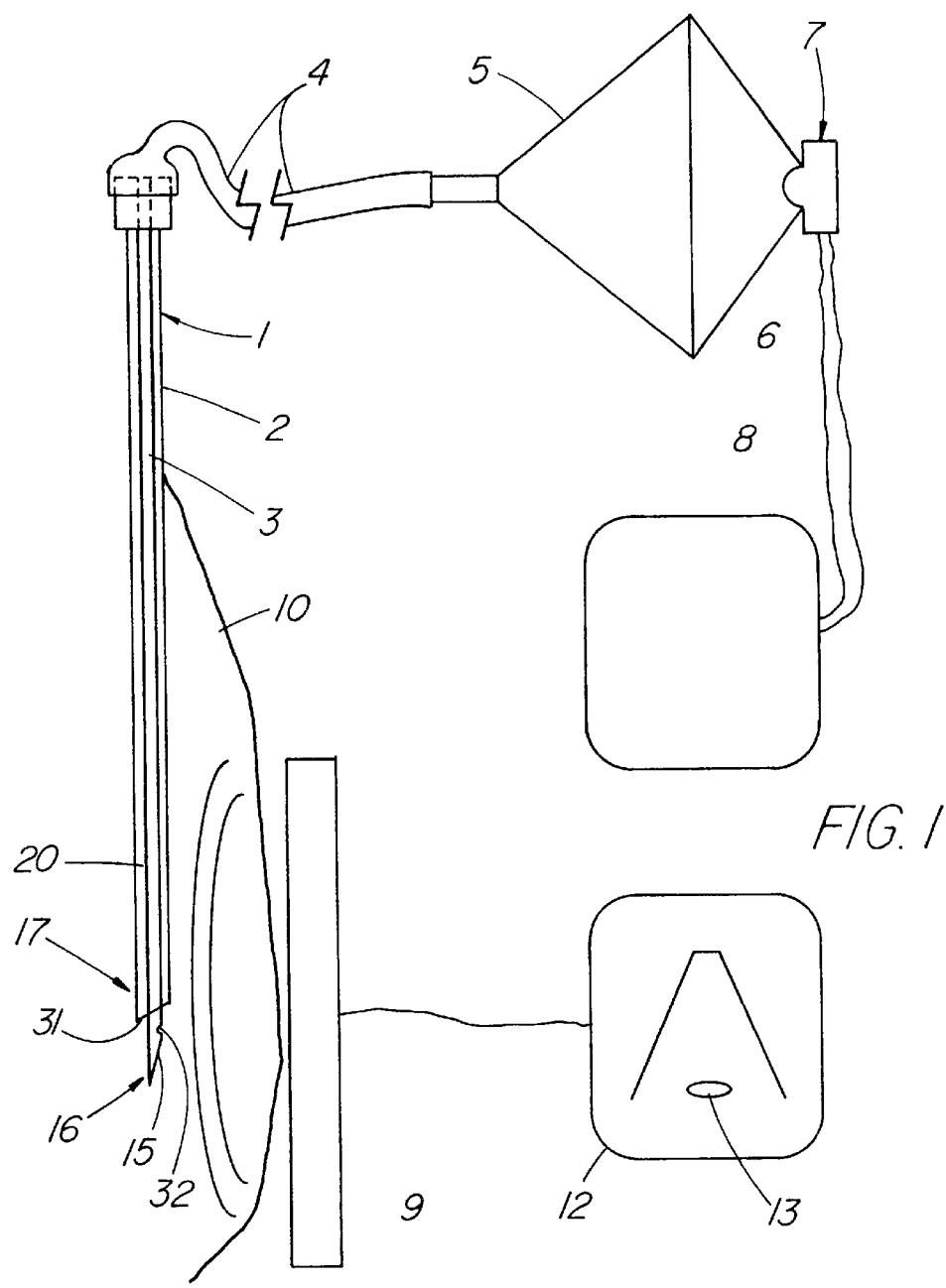
FIG. 1 is a diagrammatic representation of an ultrasonic imaging apparatus for use with a medical needle in accordance with the invention.

Referring to FIG. 1, which is a purely diagrammatic representation, a medical needle 1 is shown inserted into body tissue 10. The needle comprises a stylet 3 having an outside diameter of 0.457 mm (0.018") and housed within bore 20 of a 22 gauge tubular cannula 2 having an outside diameter of 0.711 mm (0.028"). Closed beveled tip 15 at the distal end 16 of the stylet projects about 2 mm beyond the distal end 17 and the beveled tip 31 of the cannula. The stylet is hollow and has an aperture 32 such as an eccentric opening immediately adjacent to its closed beveled tip. The eccentric opening, which protrudes beyond the distal end of the 22 gauge housing cannula, allows an oscillating air column to deliver movement to adjacent tissue but is shaped and dimensioned to minimize the possibility of body tissue entering the stylet and occluding it. This arrangement allows the tip of the stylet to be rendered visible to Doppler ultrasound during the insertion of the needle through tissue. Eight millimeter flexible pressure tubing 4 connects the hollow stylet with the neck of a funnel member 5 as shown. The mouth of funnel member 5 is coupled in an airtight manner to a moving coil loudspeaker 7 whose diaphragm 6 is driven by a signal from a signal generator 8.

Preferably, the signal, which may be a pulsed or an oscillating signal, has a period of 0.03 s to 0.001 s. More preferably, the signal has a sine, square or triangular waveform of frequency 333 Hz to 1 kHz (ideally 400 to 800 Hz, e.g., 600 Hz) and a power of a few (e.g. 100) mW.

The body tissue is insonated with an ultrasonic beam 11 by a Doppler ultrasound imager 9, which may for example be an Acuson 128 XP10 imager. An image 13 of the needle tip is formed on a screen 12 of the imager.

The optimum frequency of the longitudinal oscillation generated by the transducer of the needle arrangement will depend on the Color Doppler ultrasonic imager with which it is being used, in particular on the velocity range detectable by the imager. In a typical Color Doppler ultrasonic imager, the minimum detectable velocity will be of the order of ±0.001 m/s and a maximum velocity of about ±3.8 m/s, with a more usual range being from ±0.02 m/s to ±0.6 m/s. Accordingly, it is believed that the frequency and amplitude of oscillation should be such that the maximum velocity is within the above ranges. With conveniently achievable amplitudes of oscillation, it is believed that the most useful frequencies will be in the audio range, i.e., 20 Hz to 20 kHz, but the invention is by no means limited to stylets suitable for the above ranges.

By way of example, a working model of the needle utilizing a jelly phantom in place of the body tissue 10 was constructed generally as shown in FIG. 1. The components of the working model were as follows: hollow cannulas, a hollow stylet, a loudspeaker, signal generator and 50 cm of 'pressure' tubing. The cannulas were standard 15 cm Chiba needles (Cook Inc., Bloomington, Ind.) in 18, 20, and 22G sizes, and the 15 cm hollow stylet was made of superelastic nickel titanium alloy with an inner diameter of 0.406 mm (0.016") (Raychem Corp., Menlo Pk. Calif.). The speaker coil was modified from a 127 mm (5 inch) diameter plastic-coned loudspeaker (Tannoy Ltd., Strathclyde, Scotland) and was connected in an airtight arrangement via a funnel to the hollow stylet. The signal generator used was a Korg 770 synthesizer (Keio Electronic Laboratory Corporation, Tokyo, Japan). This instrument generates square, triangular and rectangular waveforms at a wide range of audio frequencies. The signal was amplified through a Realistic SA 1500 audio amplifier (Tandy Corporation, Fort Worth, Tex.).

Color Doppler ultrasound machines used to evaluate the needle were an Acuson XP10 (Acuson Ltd.), and a Diasonics Spectra VST (Diasonics Ltd. Milipitas, Calif. USA). Testing was done by applying a 3.5 MHZ probe to a jelly phantom and immobilizing it in position. The pressure tubing was then connected directly to the needle barrel (minus its matching solid stylet). The needle was then inserted into the phantom as far as possible. Probes of 5 MHz and 7.5 MHz were also used with the needle with similar results. Signal was applied to the needle starting at 1 Hz and gradually increasing in frequency until color signal was registered by the ultrasound machine at a selected pulse repetition frequency and gain setting.

The following results were observed. The needle tip was displayed as a beacon of color regardless of the angle of incidence of the Doppler beam. Transverse, longitudinal and oblique projections displayed the beacon equally. The color signal was not constant but was found to change hue and to flicker at varying rates depending on the frequency of the sound wave applied to the needle. This is believed to be caused by an interference pattern at the needle tip between the frequency of motion and the pulse repetition frequency of the incoming Doppler wave. The needle tip was readily detectable when inserted fully into the phantom. This corresponded to a depth of 15 cm. No signal other than that at the tip of the needle was registered when the needle was stationary.

It was found that a frequency of 600 Hz yielded a beacon of signal, which was readily detectable at pulse repetition frequencies ranging from 800 to 2250 kHz using the Diasonics machine. Within this range, color gain values of between 68 and 80 dB were required to demonstrate a visible beacon unaccompanied by color noise on the screen. There was no visible difference between sine, square, triangular or rectangular waveforms. Many other frequencies were found to generate detectable signal at various pulse repetition frequencies and color gain settings, but 600 Hz was the single frequency most likely to be detectable in the range of pulse repetition frequencies described.

Increasing gain values above 80 dB led to color noise which could be mistaken for the needle tip. Below a pulse repetition frequency of 800 kHz useful signal at the tip uncorrupted by color noise was demonstrated only at 400 Hz with this particular apparatus. Above 2,250 Hz, a similar problem occurred with this particular apparatus. Because pulse repetition frequencies are not given a numerical value on the Acuson XP10 display, it was not possible to directly correlate the findings between it and the Diasonic Spectra VST. It was found that the Acuson machine was capable of displaying the color beacon at the tip of the needle as well as the Diasonics although differences in frequency response between these two machines could not be ruled out because the frequency of pulse repetition is not displayed on the Acuson machine.

At higher pulse repetition frequencies (greater than 1000 Hz), tissue motion 'flash' was not prominent and did not obscure the signal at the needle tip when Doppler interrogation was performed during the process of needle insertion. At pulse repetition frequencies lower than 1000 Hz, an increasing amount of tissue flash was seen with needle movement, which at the lowest settings, e.g., 100 Hz was very prominent.

It was found that when a tissue or agar phantom was used, the needle accumulated material within it and became blocked during insertion. When this occurred, no color signal was visible at the tip. Blockage was prevented by using a phantom made of ultrasound coupling jelly.

The 0.406 mm (0.016") internal diameter hollow stylet was connected to the pressure tubing and inserted into the 20G Chiba needle so that it protruded just beyond its tip to see if it was possible to conduct a signal down a lumen of this diameter. Satisfactory color signal was easily visible at the tip of this hollow stylet, although the size of the beacon was smaller than when the 20G needle barrel was connected directly to the pressure tubing.

The volume control of both amplifier and signal generator needed to be a maximum in order for good quality signal to be registered. Accordingly, the speaker was housed in a cabinet to minimize unwanted sound output. Reducing the volume caused a corresponding reduction in color signal on the monitor. Of interest is the observation that slight movement of the transducer off the needle tip resulted in failure to detect any signal. This sensitivity allowed detection of the exact location of the tip of the needle in both color Doppler and spectral modes. Furthermore, the needle tip could be easily found when the probe was displaced far away from the insertion site and aligned randomly with respect to the needle shaft.

Figure 2:
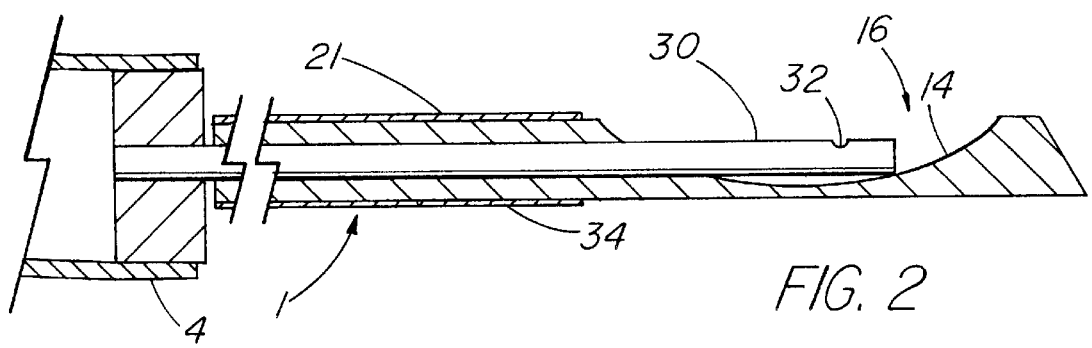
FIG. 2 is a longitudinal cross-section of another needle in accordance with the invention for use in the arrangement of FIG. 1.

Referring now to FIG. 2, another needle arrangement is shown designed to prevent occlusion of the oscillating fluid column during insertion into the body tissue and comprises a tubular outer cutting sheath 34 housing a trocar 21. Trocar 21 has a recess 14 at its distal end which exposes a retractable tubular stylet 30 which has a radially directed aperture 32 adjacent its (distal) end 16. The bore of stylet 30 communicates with the funnel arrangement shown in FIG. 1 via flexible tubing 4 and consequently the Doppler signal is emitted at aperture 32 throughout the insertion and enables the precise position of the tip portion of the needle arrangement to be detected continuously. In a variant, two, three or more smaller apertures regularly circumferentially distributed about the forward region (e.g., the region up to 10 mm from the distal end) of the stylet can be substituted for the single aperture 32 in order to increase the strength of the stylet.

In use, first the trocar 21 is advanced (i.e., to the right in FIG. 2) together with the stylet 30, the latter having its aperture 32 located in the recess 14 as shown and the outer cutting sheath being retracted as shown. When the recess 14 has been advanced to the required position, as determined with the aid of the Doppler ultrasound image of the stylet tip region, the stylet 30 is withdrawn from the trocar 21 to allow tissue to fill the recess 14 and outer cutting sheath 34 is advanced (i.e., from left to right relative to FIG. 2) over the trocar to cut off the tissue lying in recess 14. The resulting tissue sample can then be extracted. In this manner, a tissue sample (e.g., of a liver lesion) can be taken from an accurately known region of the tissue.

FIG. 10 depicts an enlarged and sectioned side view of the distal end 16 of tubular stylet 30 of FIG. 2. Bore 18 extends longitudinally in the tubular stylet and is defined by wall 19 of the stylet. Radially directed aperture 32 extends through wall 19 and communicates with bore 18.

The needle arrangements of FIGS. 3 to 6 are similar to that of FIG. 2 except that the design of the stylet about or near the forward tip is varied. In one variation, an inclined surface 35 defines the distal tip of stylet 30. Accordingly, corresponding parts are denoted by the same reference numerals.

In the arrangement shown in FIG. 3, the aperture is defined by a channel 32$^A$ of rectangular cross-section cut in the upper surface of the wall of the hollow stylet 30.

In the needle arrangement shown in FIG. 4, the aperture is defined by a channel 32$^B$ of rectangular cross-section cut in the upper surface of the wall of the hollow stylet 30. The sides of the channel 32$^B$ are convex, and the base of the channel is concave, so that the transverse cross-section of the channel has a gradual convex transition with the adjacent forward portion of the exterior surface of the cylindrical wall. The resulting aperture is, therefore, less likely to cut tissue as it is advanced.

In the needle arrangement shown in FIG. 5, the aperture is in the form of one or a plurality (e.g., 3) of longitudinal slits 32$^C$ of length 5 mm and width 100 micrometers which are spaced regularly around the forward region of the circumference of the stylet.

In the arrangement shown in FIG. 6, a plurality (e.g., 5 or more) of circular apertures 32$^D$ are provided. They are suitably of diameter 100 micrometers and can be formed by laser beam perforation of the stylet wall, for example. In a particularly preferred embodiment there are 15 apertures of diameter 127 micrometers (0.005 inches) formed by laser beam perforation of the stylet wall.

The needle arrangement shown in FIG. 7 comprises a solid stylet 130 having an expanded distal tip 133 of circular transverse cross-section with an inclined flat face 135, the face 135 having a cutting edge at its periphery, and a cannula 140 whose cylindrical bore is of a slightly greater diameter than that of the distal tip of the stylet. The outer edge region 142 of the mouth of the cannula is rounded to prevent it from cutting tissue and a radial aperture 132 is defined by the gap between the mouth of the cannula and the distal tip of the stylet. The proximal end of the cannula 140 has a radial port 141 which communicates with its bore and can be attached to the flexible tubing 4 of the apparatus shown in FIG. 1 to provide sub-ultrasonic emission from aperture 132. The proximal end 131 of the stylet 130 protrudes from and, in the position shown in FIG. 7, seals the proximal end of the cannula 140 but can be retracted to withdraw the stylet from the cannula after the tip region of the assembly has been located by the Doppler ultrasound apparatus of FIG. 1.

The needle arrangement shown in FIG. 8 comprises an aspiration biopsy (Chiba) needle 40 and a hollow tubular stylet 30 with a non-cutting aperture 32$^E$, which is housed within the needle 40. Inclined surface 35 defines the distal tip of tubular stylet 30. The periphery of the aperture 32$^E$ is smoothly rounded to prevent occlusion by tissue and the bore 18 of the stylet is connected to the flexible tubing 4 of the apparatus shown in FIG. 1 to provide sub-ultrasonic emission from aperture 32$^E$.

The needle arrangement shown in FIG. 9 comprises an aspiration biopsy (Chiba) needle 40 and a hollow tubular stylet 30 with a non-cutting aperture 32$^F$, which is housed within the needle 40. Inclined surface 35 defines the distal tip of tubular stylet 30. The periphery of the aperture 32$^F$ is smoothly rounded and faces rearwardly to prevent occlusion by tissue, and the bore 18 of the stylet is connected to the flexible tubing 4 of the apparatus shown in FIG. 1 to provide sub-ultrasonic emission from aperture 32$^F$.

In all the arrangements illustrated in the drawings, the stylet, cannula and trocar (if used) as well as the flexible tubing are sterilized and can be disposable.

The invention also provides a medical needle which is adapted for insertion into body tissue, the needle being provided with a transducer which is substantially mechanically isolated from the needle and coupled to a fluid column within the needle, the transducer being arranged to generate a longitudinal oscillation of said fluid column at a non-ultrasonic frequency which enhances the visibility of the needle tip to Doppler ultrasound imaging.

The invention also extends to every novel combination or sub-combination disclosed herein.

What is claimed is:

1. A medical needle (1) comprising:
a stylet (3, 30) having a bore (18) extending longitudinally therein, a distal end (16), a wall (19) positioned about said bore and an aperture (32, 32$^{A-F}$) in said wall about said distal end, wherein said aperture communicates with said bore and is located and dimensioned to substantially prevent occlusion of said aperture by body tissue when inserted therein.

2. A medical needle as claimed in claim 1 wherein said aperture is a radial aperture (32).

3. A medical needle as claimed in claim 1 wherein said aperture is a transverse channel (32$^A$) cut into a cylindrical wall (19) of said needle.

4. A medical needle as claimed in claim 1 wherein said aperture is a transverse channel (32$^B$) cut into a cylindrical wall (19) of said needle and wherein a transverse cross-section of said channel has a gradual convex transition with an adjacent forward portion of an exterior surface of said cylindrical wall.

5. A medical needle as claimed in claim 4 wherein said transverse cross-section has a concave base portion.

6. A medical needle as claimed in claim 1 comprising a plurality of apertures formed as longitudinal slits (32$^C$).

7. A medical needle as claimed in claim 1 comprising a plurality (32$^D$) of apertures positioned about said distal end.

8. A medical needle as claimed in claim 7 wherein said apertures are laser perforations of said wall.

9. A medical needle as claimed in claim 7 wherein at least one of said apertures comprises a longitudinally extending slit in said wall.

10. A medical needle as claimed in claim 1 wherein a smallest dimension of said aperture is no greater than 2 mm.

11. A medical needle as claimed in claim 1 wherein said aperture comprises a longitudinally extending slit (32$^C$) in said wall.

12. A medical needle as claimed in claim 1 wherein said needle is sterilized.

13. A medical needle as claimed in claim 1 further comprising a cannula (2) having a bore (20) in which said stylet is located.

14. A needle as claimed in claim 1 wherein said needle further comprises a trocar (21) having a bore extending longitudinally therein and a recess (14) about a closed distal end thereof and wherein said stylet is positionable in said bore of said trocar to expose said aperture of said stylet.

15. A needle as claimed in claim 13 further comprising an outer cutting sheath (34) in which said trocar is housed therein.

16. A medical needle as claimed in claim 1 wherein said aperture is a non-cutting aperture (32$^E$).

17. A medical needle as claimed in claim 1 wherein said aperture is a non-cutting aperture (32$^F$) having a periphery that is smoothly rounded and faces rearwards to prevent occlusion by tissue.

18. A medical needle (1) comprising a cannula (140) and a stylet (130) positioned within a bore (20) of said cannula, said stylet having an expanded distal tip (133) which tip has a transverse cross-section generally complementary to that of said bore of said cannula so as to substantially prevent the occlusion by body tissue of a distal end of said cannula in use, said stylet being advanceable relative to said cannula to define a radial aperture (132) between said tip and said distal end of said cannula which communicates with said bore of said cannula.

* * * * *